ns009784712B2

United States Patent
Persson et al.

(10) Patent No.: US 9,784,712 B2
(45) Date of Patent: Oct. 10, 2017

(54) SPLIT-RING RESONATOR PLASMA SOURCE

(71) Applicants: Anders Persson, Uppsala (SE); Greger Thornell, Uppsala (SE); Martin Berglund, Uppsala (SE)

(72) Inventors: Anders Persson, Uppsala (SE); Greger Thornell, Uppsala (SE); Martin Berglund, Uppsala (SE)

( * ) Notice: Subject to any disclaimer, the term of this patent is extended or adjusted under 35 U.S.C. 154(b) by 129 days.

(21) Appl. No.: 14/896,363

(22) PCT Filed: Jun. 5, 2014

(86) PCT No.: PCT/IB2014/003264
§ 371 (c)(1),
(2) Date: Dec. 4, 2015

(87) PCT Pub. No.: WO2015/114402
PCT Pub. Date: Aug. 6, 2015

(65) Prior Publication Data
US 2016/0123927 A1    May 5, 2016

Related U.S. Application Data

(60) Provisional application No. 61/831,678, filed on Jun. 6, 2013.

(51) Int. Cl.
*G01R 27/04*    (2006.01)
*G01R 27/32*    (2006.01)
(Continued)

(52) U.S. Cl.
CPC .......... *G01N 27/628* (2013.01); *G01N 27/02* (2013.01); *H01J 37/32935* (2013.01);
(Continued)

(58) Field of Classification Search
CPC . G01N 27/628; G01N 27/02; H01J 37/32935; H05H 1/46; H05H 1/2406;
(Continued)

(56) References Cited

U.S. PATENT DOCUMENTS 5,545,985 A * 8/1996 Campbell .............. G01D 5/145
324/207.21
7,969,148 B2 * 6/2011 Noguchi ................ G01D 5/145
324/207.21
(Continued)

OTHER PUBLICATIONS

International Preliminary Report on Patentability and Written Opinion of the International Searching Authority for PCT/US2014/003264, mailed Dec. 17, 2015, 15 pages.
(Continued)

*Primary Examiner* — Giovanni Astacio-Oquendo
(74) *Attorney, Agent, or Firm* — The Marbury Law Group PLLC (57) ABSTRACT

A miniaturized plasma source includes a stripline split-ring resonator. The split-ring resonator is sandwiched between two dielectric substrates and two metal ground planes. In order to make the plasma accessible from the outside of the ground planes, a hole is made through the gap between the ends of the split ring. The two ground planes act as an electromagnetic shield, protecting the split-ring resonator from electromagnetic interference due to changes in the electric or dielectric environment surrounding it. The miniaturized plasma source is particularly useful in optogalvanic spectroscopy applications.

23 Claims, 7 Drawing Sheets

(51) Int. Cl.
    *G01N 27/62* (2006.01)
    *H05H 1/24* (2006.01)
    *G01N 27/02* (2006.01)
    *H01J 37/32* (2006.01)
    *H05H 1/46* (2006.01)
    *H05H 1/48* (2006.01)

(52) U.S. Cl.
    CPC ............ H05H 1/2406 (2013.01); H05H 1/46 (2013.01); *H05H 2001/2418* (2013.01); *H05H 2001/4645* (2013.01); *H05H 2001/481* (2013.01)

(58) Field of Classification Search
    CPC ... H05H 2001/4645; H05H 2001/2418; H05H 2001/481
    USPC .......................................... 324/629, 600, 602
    See application file for complete search history.

(56) References Cited

U.S. PATENT DOCUMENTS

2004/0016305 A1* 1/2004 Matsumoto ............. G01L 5/221
    73/862.331
2007/0170996 A1 7/2007 Dutton et al.

OTHER PUBLICATIONS

International Search Report and written Opinion for PCT/US2014/003264, mailed Oct. 12, 2015.

Tran, T. H. et al., "Atmospheric pressure microplasma source based on parallelstripline resonator," Current Applied Physics, North-Holland, Amsterdam, NL, vol. 11, No. 5, Apr. 28, 2011 (Apr. 28, 2011),pp. S126-S130 XP028111305,ISSN: 1567-1739, DOI:10.1016/J.CAP.2011.04.049 [retrieved on May 14, 2011] p. s127, left-hand column, line 6-line13 figure 1.

Hopwood, J. et al., "Low-power microwave plasma source based on a microstrip split-ring resonator", IEEE Transactions on Plasma Science, IEEE Service Center, Piscataway, NJ, US, vol. 31, No. 4, Aug. 1, 2003 (Aug. 1, 2003), pp. 782-787, XP011099886, ISSN: 0093-3813, DOI:10.1109 TPS.2003.815470 figures 1,4 p. 782, right-hand column, line 1-line 23 p. 784, left-hand column, line 6—p. 785, left-hand column, line 2.

Miura, N. et al., "Spatially resolved argon microplasma diagnostics by diode laser absorption", Journal of Applied Physics, American Institute of Physics, US, vol. 109, No. I, Jan. 10, 2011 (Jan. 10, 2011), pp. 13304-1-13304-6, XP012146640, ISSN: 0021-8979, DOI: 10.1063/1.3531557 pp. 13304-2, right-hand column, line 5-line 44; figures 1-2 pp. 13304-4, right-hand column, line 14-line 16.

Barbieri, B. et al., "Optogalvanicspectroscopy",Reviews of Modern Physics, American Physical Society, US, vol. 62, No. 3, Jan. 1, 1990 (Jan. 1, 1990), pp. 603-644, XP000916046,ISSN: 0034-6861, DOI: 10.1103/REVMODPHYS.62.603 abstract.

Eilers, G. et al., "The Radiocarbon Intracavity Optogalvanic Spectroscopy Setup at Uppsala," Proceedings of The 21st International Radiocarbon Conference, vol. 55, No. 2-3,Jan. 1, 2013 (Jan. 1, 2013), pp. 237-250, XP055203782, ISSN: 0033-8222 figures 1-2 abstract p. 237-p. 240 p. 244.

* cited by examiner a)

SPLIT-RING RESONATOR PLASMA SOURCE

CROSS-REFERENCE TO OTHER APPLICATIONS

This application is a national phase application under 35 U.S.C. §371 of international application PCT/IB14/003264, filed Jun. 5, 2014 which claims the benefit of priority to U.S. Provisional Application No. 61/831,678 filed on Jun. 6, 2013, the entire teachings of which are incorporated herein by reference.

FIELD OF THE INVENTION

The present invention relates to a miniaturized plasma source, and in particular a split-ring resonator and a laser spectroscopy device comprising such.

BACKGROUND

Miniaturized plasma sources are used in a variety of applications, e.g., in chemical analysis, for sterilization or activation of different substances, or as ion sources. Some of their advantages are low power consumption, simple design and fabrication, mechanical robustness, long lifetime, high non-thermal plasma density, and the ability to operate at atmospheric pressure, although they also suffer from some limitations.

Figure 1A:
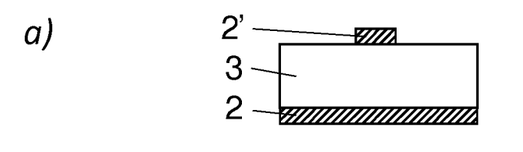
FIG. 1(a) is a side cross sectional view through a prior art MSSR plasma source.
Figure 1B:
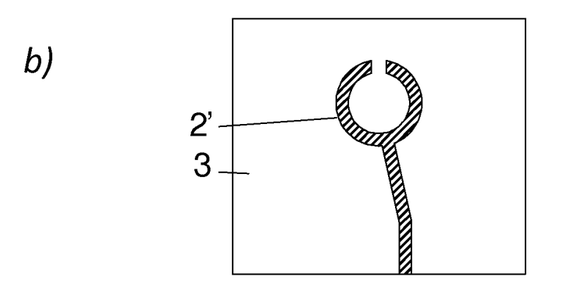
FIG. 1(b) is an overhead view of a prior art MSRR plasma source.

Miniaturized plasma sources based on microstrip split-ring resonators (MSRRs) have received an increasing amount of interest during the last decade. A microstrip is a radio frequency transmission line consisting of a dielectric substrate sandwiched between a metal strip and a metal ground plane, as shown in FIG. 1(a). In the case of an MSRR, the metal strip is a dipole folded into a circle, with the two ends creating a small gap, as shown in FIG. 1(b), over which an electric field can be created. Here, the dipole corresponds to a half-wavelength microwave resonator often used as an antenna. The dipole is connected to an additional microstrip transmission line, a feed line that supplies it with radio frequency (RF) power.

Figure 1C:
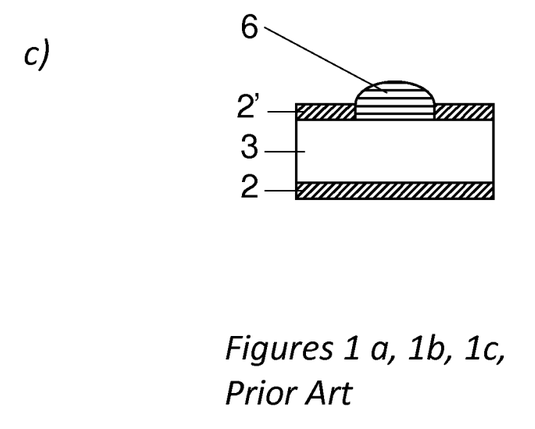
FIG. 1(c) is a side cross sectional view of part of a prior art MSRR plasma source with plasma in the gap.

At resonance, the electric potential at the ends of the dipole is 180° out of phase, enabling the amplitude of the electric field between them to be amplified several orders of magnitude. Hence, with a relatively low input power, a large potential is created over the gap, and this potential is used to ignite and maintain a plasma, as shown in FIG. 1(c). The large potential arises because when a standing wave is created in a dipole, the current is zero at the endpoints and at its maximum at the middle of the strip. Correspondingly, the electric potential is at its maximum and minimum, respectively, at the endpoints, although the two ends are 180° out of phase, and zero at the middle.

The electric field in a microstrip is mostly confined to the dielectric substrate. However, in the gap of a split-ring resonator, the electric field between the ends of the folded dipole is elevated from the substrate and is concentrated in the plane between the two ends. This provides one of the key features of the MSRR, i.e., that most of the electric field is concentrated to the gap. It should be noted that no DC potential is applied to the plasma, minimizing energy lost to moving ions.

In order to effectively operate the MSRR, the input impedance of the ring should match the impedance of the feed line. The characteristic impedance of the ring depends on the offset of the feed line from the center of the dipole, and the quality factor of the microstrip.

One laser spectroscopy technique using a plasma source is optogalvanic spectroscopy (OGS) in general and intracavity optogalvanic spectroscopy (ICOGS) in particular. Both are based on the optogalvanic (OG) effect. Using this, the interaction of an incident laser beam with atoms or molecules present in a plasma induces changes in the electrical properties (e.g., voltage or impedance) of the plasma which can be measured electrically. The measured impedance change is proportional to the number of interacting molecules but will also depend on the plasma parameters, e.g., pressure, as well as the laser intensity and gas composition in the discharge.

Figure 2:
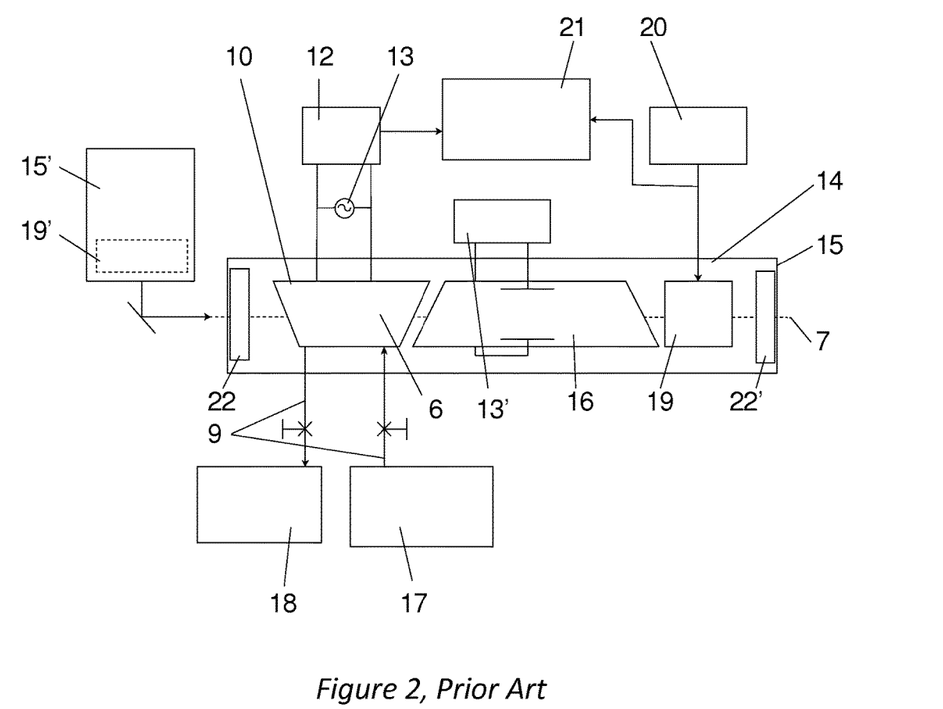
FIG. 2 is a schematic illustration of a prior art intracavity optogalvanic spectroscopy (ICOGS) system.

By using an isotope-specific $CO_2$ laser as the source of the radiation, i.e. a laser with a wavelength identical to one of the isotope-specific transitions in the mid-IR spectrum of $CO_2$, it has been shown that OGS can be applicable to measurements of the isotopic composition of carbon-containing samples, e.g., the $^{13}C/^{12}C$ ratio, for, e.g., ulcer diagnostics, and that it might even be possible to measure the $^{14}C/^{12}C$ ratio using the ICOGS technique. The schematic of a standard ICOGS system is shown in FIG. 2. As shown in FIG. 2, a sample cell 10 is inserted into the laser cavity 14 of a laser 15, with a lasing frequency corresponding to a transition in the spectrum of the active laser medium 16 (which may be a moiety of interest, e.g, a gas mixture for a $CO_2$ laser) which receives a potential from power source 13', which may be different from the power source 13 which drives a plasma 6 in the sample cell 10. A sample can be inserted into the sample cell 10, via a fluidic system 9, from an analyte source 17. The pressure in, or the flow through, the sample cell 10 is defined by a vacuum pump 18. The sample cell 10 and the active laser medium 16 are located between two reflectors 22 and 22' in the cavity 14 of the laser 15, where the first reflector 22 can be an output coupler and the second reflector 22' can be a grating. A shutter 19 connected to a modulator 20 chops the laser beam 7, creating a frequency dependent optogalvanic response in the sample cell 10, which is measured by a detector 12, connected to the power source 13. The measured signal is demodulated in a signal processing unit 21 triggered by the modulator 20, yielding the optogalvanic signal. For quantitative measurements, the sample cell 10 is illuminated by a second laser beam from a reference laser 15'. The reference laser 15' has a separate shutter 19', operating at a different frequency than the shutter 19 of the laser 15 with the laser medium 16. Two optogalvanic responses are measured by the detector 12, and demodulated by the signal processing unit 21 into two unambiguous optogalvanic signals.

In ordinary OGS, the ionized sample is located in the laser beam path, i.e. outside the laser, whereas in ICOGS the sample is inserted into the laser cavity itself. In both cases, the analyzed carbon is in the form of $CO_2$. The intracavity approach has been suggested to increase the sensitivity by almost seven orders of magnitude compared with ordinary "extracavity" OGS. However, in many applications, the sensitivity of extracavity OGS is sufficient, and the plasma source can be kept outside the laser. A spectrometer for extracavity OGS of $^{13}C/^{12}C$ ratios is sometimes referred to as a laser-assisted ratio analyzer (LARA).

SUMMARY

Embodiments include a plasma source that includes a split-ring resonator having a first side and a second side, a first dielectric material having a first side facing the first side of the split-ring resonator and a second side opposite to the first side, a first electrically conductive ground plane facing the second side of the first dielectric material, a second dielectric material having a first side facing the second side of the split-ring resonator, and a second electrically conductive ground plane facing the second side of the second dielectric material.

Further embodiments include an optogalvanic spectroscopy system that includes a laser and a split ring resonator plasma source.

Further embodiments include an optogalvanic spectroscopy system that includes a laser, a detector, a split-ring resonator plasma source having a gap, at least one probe located in the gap of the split-ring resonator, a probe connection connecting the at least one probe to the detector, and a power source connection separate from the probe connection connecting the split-ring resonator to the power source.

Further embodiments include an optogalvanic spectroscopy method that includes generating a plasma in a gap of a split-ring resonator plasma source, such that an analyte is located in the plasma in the gap, providing laser radiation through the analyte located in the plasma in the gap, and detecting at least one electrical property of the plasma.

Further embodiments include a detection method that includes providing power from a power source through a power source connection to a split-ring resonator plasma source to generate a plasma in a gap of a ring of the split-ring resonator, and detecting at least one electrical property of the plasma in the gap using at least one probe connected to a detector using a probe connection separate from the power source connection.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

FIGS. 1(a) to 1(c) illustrate a prior art microstrip split ring resonator (MSRR) plasma source, wherein

FIGS. 3(a) to 3(f) illustrate a stripline split ring resonator (SSRR) plasma source according to an embodiment, wherein

FIGS. 8(a) and 8(b) are top views of the central portions of a respective split-ring resonator containing part (FIG. 8(a)) and a countersink containing part (FIG. 8(b)) of a stripline split-ring resonator in a spectroscopy system according to an embodiment.

FIG. 8(c) is a close-up view of the split-ring resonator of FIG. 8(a) illustrating the position of probes with respect to a plasma in a hole.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Various embodiments are directed to a miniaturized plasma source, and in particular a miniaturized split-ring resonator plasma source. Further embodiments include a laser spectroscopy system comprising a miniaturized plasma source, and laser spectroscopy methods using a miniaturized plasma source.

The inventors have discovered that although prior art microstrip split-ring resonators (MSRRs) possess a number of advantages as summarized above, they also suffer from some major disadvantages. From a miniaturization and integration point of view, the most severe limitation of MSRRs stems from their intrinsic design. An MSRR is designed with certain assumptions regarding the electric and dielectric environment surrounding it. Most often the microstrip is assumed to have the dielectric substrate and the ground plane beneath it and free space above. This opposes one of the most common motivations for miniaturizing a system, namely the enabling of high-level integration, in turn facilitating the construction of mobile or even handheld devices. An MSRR in an integrated system is not only sensitive to what other components are stacked on top of, or mounted close to, the dipole, but also to where the device is operated, since such variations will, to some extent, contradict the initial assumption regarding the dielectric environment. Although the effect of stationary parts could be accounted for, a device with integrated MSRRs would not be compatible with moving parts such as valves or pistons, since these would make the dielectric properties of the surroundings time dependent. Uncontrolled and random sources of noise would have the same effect. This sensitivity is of course particularly problematic for devices used in field hardware, for which the environment is unknown. For example, a device placed on a table would have different resonance characteristics depending on if it is placed close to or far from, e.g., a metallic leg. Hence, MSRRs have major electromagnetic compatibility (EMC) issues.

The inventors have also discovered that another disadvantage of MSRRs is the geometry of the generated plasma. As explained above, the electrical field generating the plasma is concentrated in the plane between the ends of the dipole. Hence, the plasma will have the dielectric substrate on one side and free space on the other. This close proximity to the dielectric can be a major disadvantage in spectroscopic applications where substances or elements present also in the substrate material may be studied, since the plasma may cause erosion of the substrate, thus contaminating the sample and/or plasma and causing an erroneous analysis. Moreover, the MSRR only facilitates emission spectroscopy, where the direct emissions in the plasma are studied, but not the many kinds of laser spectroscopy, where laser light interacts with the plasma.

The inventors have also discovered that new applications of OGS, along with rising demands from the traditional clients, have created an increasing demand for more sensitive and less expensive measurement methods, and, even more important, methods that suffice with smaller samples. ICOGS can handle samples in the sub-microgram range. The limiting factor is the amount of carbon that is required to fill the plasma chamber in which the sample is ionized, to an adequate pressure. This chamber is typically a hermetically sealed cavity equipped with a plasma source for ionizing the sample, and Brewster angle windows for reflection-free transmission of the laser beam through the cell. The diameter of the laser beam, the volume of the plasma, and pressure in the chamber have proven to be important parameters for the sensitivity. In order to minimize the sample size, it would be convenient to reduce the plasma volume so that less $CO_2$ is required to keep the cavity at a certain pressure. This would, in turn, require miniaturization of the plasma source.

The inventors have also discovered that a major disadvantage of current plasma cells in ICOGS spectrometers includes their relatively large volume (typically around 30 ml), their high cost (because they are typically custom made by a professional glass-blower), and the fact that they use the same circuitry to create the plasma and to measure the OG signal (making them more susceptible to voltage noise and thermal fluctuations).

One non-limiting objective of an embodiment of the present invention is to overcome the drawbacks of MSRRs, associated with system integration and EMC. This may be achieved by creating a stripline split-ring resonator, consisting of a split-ring resonator sandwiched between two dielectric substrates and two metal ground planes. In order to make the plasma accessible from the outside of the ground planes, a hole may be made through the gap between the ends of the split ring.

In one embodiment of a stripline split-ring resonator, the two ground planes act as an electromagnetic shield, protecting the split-ring resonator from electromagnetic interference due to changes in the electric or dielectric environment surrounding it. Hence, the two ground planes may greatly improve the EMC of the stripline split-ring resonator, which may virtually maintain its resonance regardless of whether it is integrated in a system with other electrical parts, and regardless of what kind of electromagnetic environment the system is operated in.

Another non-limiting objective of an embodiment of the present invention is to avoid chemical contamination of the plasma due to plasma erosion of the dielectric substrate. In a stripline split-ring resonator according to various embodiments, the electrical field, and consequently the plasma, may be concentrated in the plane between the ends of the split-ring resonator. Hence, the plasma may form in the hole though the gap of the split ring, and not be in close proximity to the dielectric. Hence, the risk of chemical contamination of the plasma due to plasma erosion of the dielectric substrate may be greatly reduced in the stripline split-ring resonator.

Another non-limiting objective of an embodiment of the present invention is to make split-ring resonators applicable to laser spectroscopy. This requires a laser beam to be directed through the plasma, uninterrupted by the dielectric or metallic parts of the device. In a stripline split-ring resonator according to various embodiments, this may be facilitated by making the hole through the gap sufficiently wide.

Another non-limiting objective of an embodiment of the present invention is to facilitate the use of a miniaturized plasma source in an intracavity optogalvanic spectroscopy (ICOGS) system to reduce the cell volume, cost and disturbances.

In order to minimize the cell volume, in various embodiments the hole through the gap of the stripline split-ring resonator may be made into a plasma cell by sealing it with two windows, transparent to the laser beam, and equipping it with a fluidic system for introduction of the sample. By doing so, the total volume of the cell may be reduced to around 10 µl as compared with 30 ml for an ordinary plasma cell in ICOGS, i.e., three orders of magnitude smaller.

In order to reduce cost, a stripline split-ring resonator according to various embodiments may be manufactured by means of microelectromechanical systems (MEMS) technology, which is used here in the widest sense including micromachining technology, microstructure technology, and microsystems technology. MEMS technology facilitates batch processing, which can greatly reduce the cost per part. Moreover, MEMS facilitates high-precision machining, including, e.g., laser ablation, micromilling, photolithography, physical and chemical vapour deposition, wire bonding, chemical wet and dry etching, and screen printing.

In order to further reduce the noise in the OG signal, the circuitry for creating the plasma in the stripline split-ring resonator, i.e., the RF power supply, may be separated from the circuitry for measuring the signal. This may be accomplished by providing two plasma probes in the hole of the stripline split-ring resonator and connecting them to the detector through separate conductors and connectors.

Figure 5:
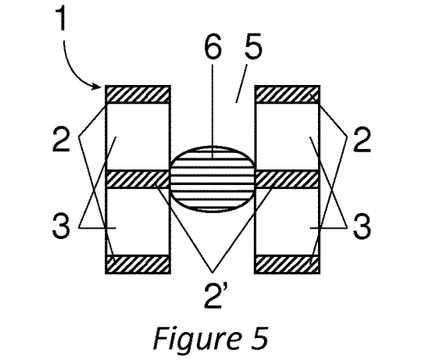
FIG. 5 is a side cross-sectional close-up view of a gap portion of a stripline split-ring resonator plasma source illustrating a cut through the source's gap and showing a geometry of the plasma in the split-ring resonator.

A miniaturized plasma source according to one embodiment of the invention is a stripline split-ring resonator plasma source 1 (alternately referred to herein as an "SSRR device" or "SSRR"), which may be made of two pieces as shown in FIGS. 3*a-f*. One piece 101 consists of a first dielectric material 3, with one side 111 of the dielectric material 3 containing a metal ground plane 2, and the other side 109 of the dielectric material 3 containing a split-ring resonator strip 2'. The split-ring resonator strip 2" comprises an electrically-conductive material, such as a metal or metal alloy. The other piece 103 consists of a second dielectric material 3 with one side 115 of the dielectric material 3 containing a metal ground plane 2 and the other side 113 of the dielectric material 3 having a countersink groove 4, in which the split-ring resonator strip 2' fits. When the pieces 101, 103 are put together (FIG. 3*c*) they make up a stripline split-ring resonator plasma source 1. In order to make the plasma 6, which is formed in the gap 2A between the two ends of the split-ring, accessible to the outside dielectric environment 3', a hole 5 may be made extending through the dielectric material 3 and the ground plane 2 in one or both of the pieces 101, 103, as illustrated in FIG. 5.

Thus, as shown in FIG. 3*a*, the "stripline" split-ring resonator 2' has a first (e.g., bottom) side 105 and a second (e.g., top) side 107. The split-ring resonator 2' comprises a split ring portion 201 having a gap 2A between the ends of the split-ring portion 201, as shown in FIG. 3*d*. The split ring portion 201 generally has a circular shape when viewed from above, as shown in FIG. 3*d*. The gap 2A in the split ring portion 201 may be filled with an electrical insulator (i.e., dielectric material).

The first (e.g., lower) dielectric material 3 has a first (e.g., top) side 109 facing the first side 105 of the split-ring resonator 2' and a second (e.g., bottom) side 111 opposite to the first side 109, as shown in FIG. 3*a*. Preferably, the first side 109 of the first dielectric material 3 contacts the first side of the split-ring resonator 2'. However, in other embodiments, additional layers or materials may be inserted between the first dielectric material 3 and the resonator 2'.

The first electrically conductive ground plane 2 faces the second (e.g., bottom) side 111 of the first (e.g., lower) dielectric material 3. Preferably, the second side 111 of the first dielectric material 3 contacts the first electrically conductive ground plane 2. However, in other embodiments, additional layers or materials may be inserted between them.

A second (upper) dielectric material 3 has a first (e.g., bottom) side 113 facing the second (e.g., upper) side 107 of the split-ring resonator 2' and a second (e.g., top) side 115 opposite to the first side 113. Preferably, the first side 113 of the second dielectric material 3 contacts the second side 107 of the split-ring resonator 2'. However, in other embodiments, additional layers or materials may be inserted between the second dielectric material 3 and the resonator 2'.

A second electrically conductive ground plane 2 faces the second (e.g., top) side 115 of the second dielectric material 3. Preferably, the second side 115 of the second dielectric material 3 contacts the second electrically conductive ground plane 2. However, in other embodiments, additional layers or materials may be inserted between them.

The first and the second dielectric materials 3 preferably comprise respective first and second electrically insulating plates (e.g., substrates). The first and second dielectric materials 3 may be made from the same or different electrically insulating materials. The first and the second electrically conductive ground planes 2 may each comprise a metal or metal alloy layer located on a second side 111, 115 of the respective first and second electrically insulating plates 3.

Figure 3:
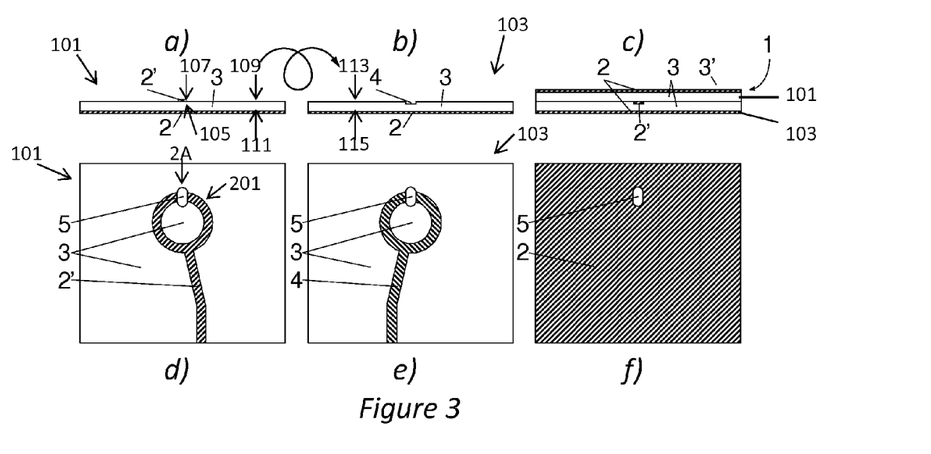
FIGS. 3(a) to 3(c) illustrate side cross sectional views of the SSRR plasma source and FIGS. 3(d) to 3(f) are top views showing the split-ring resonator containing part, a countersink containing part and the assembled device, respectively.
Figure 4:
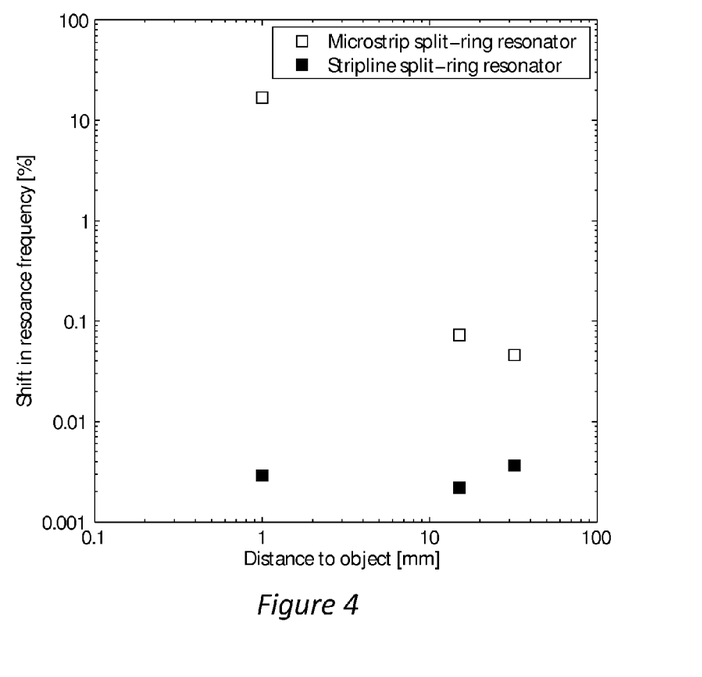
FIG. 4 is a plot illustrating experimentally obtained shifts in resonance frequency due to the proximity of a metallic object to a microstrip and a stripline split-ring resonator, respectively.

In the stripline split-ring resonator plasma source 1, the two ground planes act as an electromagnetic shield, protecting the split-ring resonator from electromagnetic interference due to changes in the electric or dielectric environment surrounding it. Hence, the two ground planes greatly improve the EMC of the stripline split-ring resonator, which may virtually maintain its resonance regardless of whether it is integrated in a system with other electrical parts, and regardless of what kind of electromagnetic environment the system is operated in. This can be seen in FIG. 4, where a metallic object was positioned at different distances from a prior art MSRR (e.g., as shown in FIGS. 1(*a*)-(*c*)) and a stripline split-ring resonator 1 according to the invention (e.g., as shown in FIGS. 3(*a*)-(*f*), respectively. It is evident that the prior art MSRR suffered from considerable shifts in the resonance frequency due to the varying electromagnetic environment, whereas the stripline split-ring resonator 1 maintained its resonance frequency regardless of the position of the object. In an application, the frequency shift would make the MSSR more difficult to ignite and operate in a stable manner, whereas the stripline split-ring resonator 1 of the invention may maintain stable operation.

Figure 6:
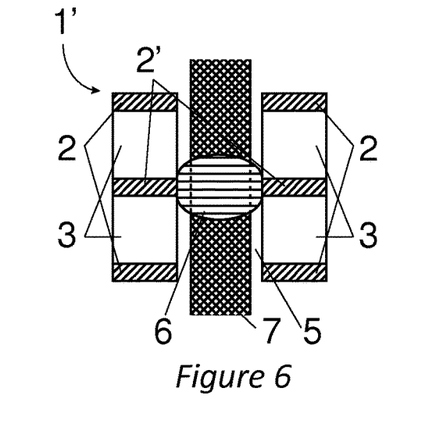
FIG. 6 is a side cross-sectional close-up view of a gap portion of a stripline split-ring resonator illustrating a cut through the source's gap and illustrating a laser spectroscopy application.

In one embodiment of the invention, the stripline split-ring resonator is used in a laser spectroscopy application 1'. In various embodiments of a laser spectroscopy system and method using a stripline split ring resonator 1, a laser beam 7 (e.g., laser radiation, such as UV, IR or visible light) may be directed through the hole 5 and the plasma 6, as illustrated in FIG. 6.

As discussed above, laser spectroscopy techniques using a plasma source and an isotope-specific $CO_2$ laser, such as optogalvanic spectroscopy (OGS) techniques in general and intracavity optogalvanic spectroscopy (ICOGS) techniques in particular, have been shown to be effective for measuring the isotopic composition of carbon-containing samples. Highly sensitive measurements of isotope ratios have a wide range of applications, from medicine to archaeology. Most renowned are, perhaps, measurements of long-lived radioisotopes such as $^{14}C$, $^{10}Be$ and $^{129}I$ that can be used for, e.g., dating organic deposits in archaeology, and rocks and sediments in geology. However, $^{14}C$ measurements have also proven useful for isotopic labeling of drugs in clinical trials by microdosing, and for studying cell regeneration in the human body.

Replacing the $CO_2$ laser with a tunable semiconductor laser with selectable center wavelength, e.g., a quantum cascade laser, may enable detection of a wide variety of molecules, in addition to $CO_2$. For example, in the ICOGS system shown FIG. 2, the active laser medium 16 may comprise a stack of semiconductor multiple quantum well heterostructures in the case of a quantum cascade laser. Examples of molecules that may be detected include different hydrocarbons and hydrogen, nitrogen and sulfur oxides, as well as more complex molecules such as explosives and drugs.

In addition to OGS and ICOGS, other spectroscopic detection schemes are possible. Examples of such techniques are cavity ring-down spectroscopy (CRDS) and integrated cavity output spectroscopy (ICOS). For the latter, off-axis integrated cavity output spectroscopy (OA-ICOS) is of particular interest. All these techniques utilize signal amplification in an optical cavity. Such a cavity consists of two highly reflective, parallel mirrors between which light is repeatedly reflected. The sample is then introduced into the cavity, making each pass of the photons add to the spectroscopic signal, which, hence, is greatly increased. The total amplification is governed by the effective path length of the photons, i.e., the mean total distance they travel inside the cavity. The effective path length is, in turn, limited by the reflectance of the mirrors as well as by intracavity absorption not relating to the sample.

In all these methods (CRDS, ICOS and OA-ICOS), the detector—commonly a mercury-cadmium-telluride IR detector—may only be placed behind the cavity. Here, the signal is still enhanced, characterized by a greatly improved SNR, but has a very low strength. More precisely, the strength of the signal outside the cavity is about $(1-R)/2$ times less than inside (R being the reflectivity of the mirrors), and, with highly reflective mirrors, this difference reaches several orders of magnitude. The low signal strength puts strict requirements on the sensitivity, and, more importantly, the noise floor of the detector, which often has to be cooled by liquid nitrogen. Moreover, the signal has to be amplified by advanced low-noise amplifiers if the full signal enhancement of the intracavity arrangement is to be obtained.

Figure 7:
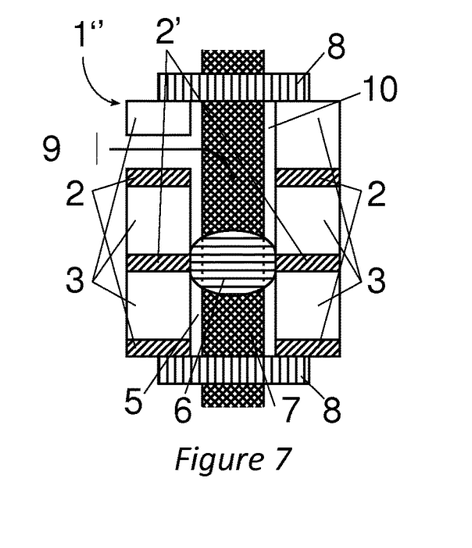
FIG. 7 is a side cross-sectional close-up view of a gap portion of a stripline split-ring resonator illustrating a cut through the source's gap and illustrates a sealed sample cell for an intracavity optogalvanic spectroscopy (ICOGC), cavity ring-down spectroscopy (CRDS), integrated cavity output spectroscopy (ICOS) or off-axis integrated cavity output spectroscopy (OA-ICOS) application.

In one embodiment of the invention, the stripline split-ring resonator is used in an optogalvanic spectroscopy (OGS) application 1". This could be any kind of OGS, and is preferably one or more of intracavity optogalvanic spectroscopy (ICOGS), laser-assisted radio analyzer (LARA), cavity ring-down spectroscopy (CRDS), integrated cavity output spectroscopy (ICOS) or off-axis integrated cavity output spectroscopy (OA-ICOS). As shown in FIG. 7, one or two laser-transparent windows 8 and a fluidic system 9 (in one embodiment a fluidic channel) may be added to the stripline split-ring resonator source 1 for laser spectroscopy applications 1'. The hole 5 through the stripline split-ring resonator 1 may be delimited by the windows 8, and may provide a miniature sample cell 10 in which the OGS measurements may be conducted. A fluidic system 9 may be used to insert the sample in the cell 10. The optogalvanic signal may be measured as the reflected power from the stripline split-ring resonator. If only one laser-transparent window is employed, the sample cell may be sealed by a mirror, or a non-transparent material.

Figure 8A:
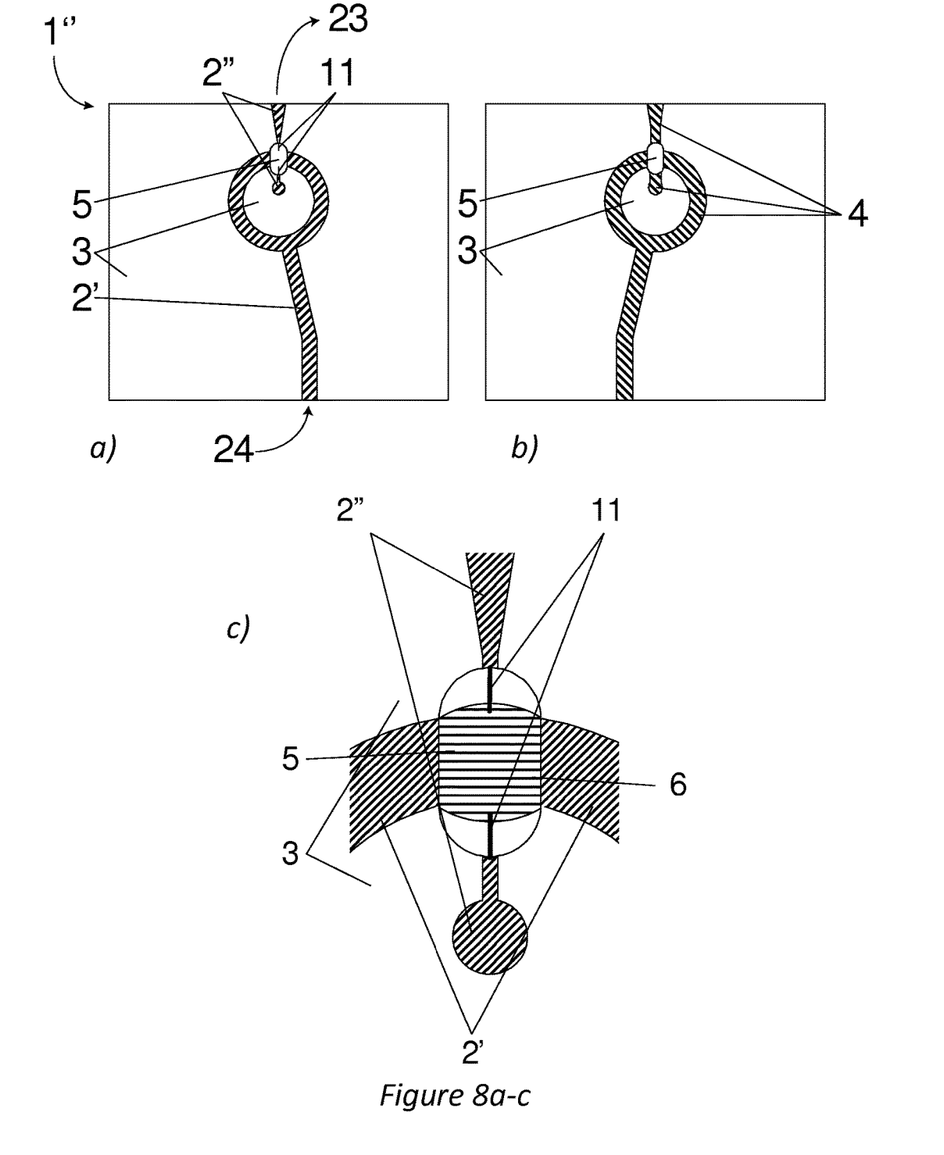

In some embodiments, one or more (e.g. two) plasma probes 11 may be added to the stripline split-ring resonator 1" as illustrated in FIG. 8, in order to measure the optogalvanic signal. In particular, at least one plasma probe 11 may be configured to monitor an electrical property of the plasma, such as plasma potential and/or impedance, or any other relevant electrical property of the plasma. The use of plasma, or Langmuir, probes 11 may be preferable since this enables more precise and accurate characterization of the plasma impedance, which is typically the measured entity in OGS, and can be used for spectroscopic signal detection in ICOGS, LARA, CRDS, ICOS and OA-ICOS.

Figure 12:
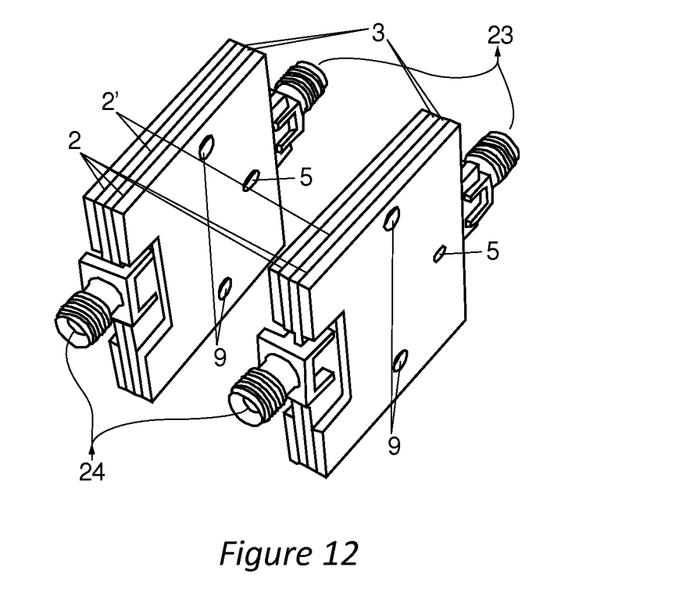
FIG. 12 is a drawing of two embodiment plasma source devices without windows, illustrating the electric and fluidic connections.

Moreover, the use of plasma probes 11 allows for separation of the detector 12 and power supply 13 of the stripline split-ring resonator 1", which is advantageous from a signal-to-noise ratio point of view, since it removes the noise of the power amplifier from the measured signal. The probes 11 may comprise electrically conductive (e.g., metal or metal alloy) leads which are extended into the plasma 6 (see FIG. 8c). The probes 11 may be contacted to two plasma probe pads 2". One of these probe pads 2" may be connected to one of the ground planes 2 of the stripline split-ring resonator 1", and the other probe pad 2" may be connected to the optogalvanic signal detector 12 via a probe connection 23, such as an inner conductor of a coaxial cable, as shown in FIGS. 8(a) and 12. The shield of the coaxial cable may be connected to the same ground plane 2 as the first plasma probe pad 2", or to the probe pad 2" directly. In contrast, a power source connection 24 (e.g., a coaxial power cable or another electrical connector) separate from the probe connection 23 may connect the split-ring resonator to the power source 13, as shown in FIGS. 8a, 9 and 12.

Figure 9:
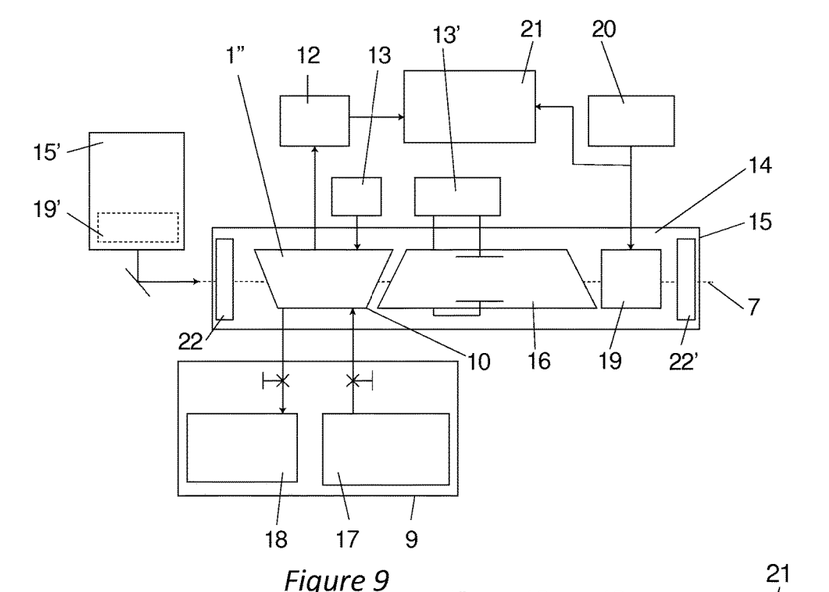
FIG. 9 is a schematic illustration of a ICOGS system containing a split-ring resonator with a separated signal detector and power supply.

In an ICOGS application, as shown in FIG. 9, the stripline split-ring resonator 1" may comprise a sample cell 10 inserted into the laser cavity 14 of a laser 15, with a lasing frequency corresponding to a transition in the spectrum of the laser medium 16 (which may be a moiety of interest, e.g., gas mixture, for a $CO_2$ laser, or a stack of semiconductor multiple quantum well heterostructures in the case of a quantum cascade laser), which is driven by a power source 13', which may be different from the power source 13 which drives a plasma in the stripline split-ring resonator 1". A sample may be inserted into the sample cell 10, via a fluidic system 9, from an analyte source 17. The pressure in, or the flow through, the sample cell 10 may be defined by a vacuum pump 18. In this embodiment, the sample cell 10 and the active laser medium 16 are located between two reflectors 22, 22' in the cavity 14 of the laser 15, where the first reflector 22 can be an output coupler and the second reflector 22' can be a grating. A shutter 19 connected to a modulator 20 chops the laser beam 7, creating a frequency dependent optogalvanic response in the stripline split-ring resonator 1", which is measured by a detector 12. The measured signal is demodulated in a signal processing unit 21 triggered by the modulator 20, yielding the optogalvanic signal. For quantitative measurements, the sample cell 10 is illuminated by a second laser beam from a reference laser 15'. The reference laser 15' has a separate shutter 19', operating at a different frequency than the shutter 19 of the laser 15. Two optogalvanic responses are now measured by the detector 12, and demodulated by the signal processing unit 21 into two unambiguous optogalvanic signals. This ICOGS setup is unique in that the sample cell 10 is a stripline split-ring resonator 1", and that the power supply 13 is separated from the detector 12. In extracavity optogalvanic spectroscopy, e.g., LARA, the stripline split-ring resonator 1" constituting the sample cell 10 may instead be located outside the laser 15 in the path of the laser beam 7, so that the beam passes through the hole 5.

Figure 10:
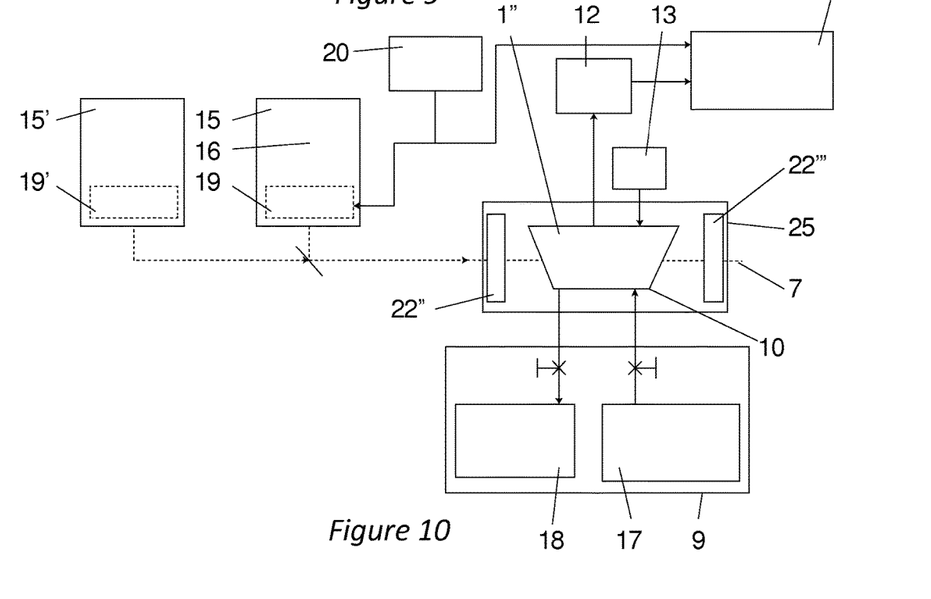
FIG. 10 is a schematic illustration of a CRDS, ICOS or OA-ICOS system containing a split-ring resonator with a separated signal detector and power supply.

FIG. 10 schematically illustrates an CRDS, ICOS or OA-ICOS application. In this embodiment, the stripline split-ring resonator 1" constitutes a sample cell 10 inserted into an optical cavity 25 consisting of two parallel reflectors 22" and 22''', which can be highly reflective mirrors. Light from a laser 15 with a lasing frequency corresponding to a transition in the spectrum of laser medium 16 (which may be a moiety of interest, e.g., gas mixture, for a $CO_2$ laser, or a stack of semiconductor multiple quantum well heterostructures in the case of a quantum cascade laser) is directed into the optical cavity 25, and reflected back and forth between the cavity reflectors 22" and 22'''. A sample can be inserted into the sample cell 10, via a fluidic system 9, from an analyte source 17. The pressure in, or the flow through, the sample cell 10 may be defined by a vacuum pump 18. The sample cell 10 is located between the two mirrors 22' and 22''' in the optical cavity 25 separate from the laser 15. A shutter 19 connected to a modulator 20 chops the laser beam 7, creating a frequency dependent optogalvanic response in the stripline split-ring resonator 1", which is measured by a detector 12. The measured signal is demodulated in a signal processing unit 21 triggered by the modulator 20, yielding the optogalvanic signal. For quantitative measurements or measurements of more than one molecular species, the sample cell 10 may be illuminated by additional laser beams from one or more reference lasers 15'. Each reference laser 15' may have a separate shutter 19', operating at a different frequency than the shutter 19 of the laser 15. Two optogalvanic responses are now measured by the detector 12, and demodulated by the signal processing unit 21 into two unambiguous optogalvanic signals. CRDS, ICOS or OA-ICOS may also utilize plasma probes 11 which allows for the separation of the power supply 13 from the detector 12.

An advantage of the optogalvanic sensor using a stripline split-ring resonator according to various embodiments is its transparency to the incident radiation (e.g., laser) beam. Conventional absorption spectroscopy sensors measure the signal by collecting photons. Hence, placing such a sensor inside an optical cavity would block the beam-path, and remove any intracavity enhancement effects. The sensor of the present invention, on the other hand, does not absorb photons apart from those that interact with the sample gas. Instead, it measures the effect of such interactions on the impedance of the plasma. Hence, the sensor can be placed inside the cavity without blocking the beam. Inside the cavity, the signal enhancement may be characterized by increased signal strength instead of improved SNR. In other words, embodiments of the present invention may enable access to the amplification as increased signal, instead of reduced noise, which is much easier to measure, and, consequently, the cavity enhancement can be utilized without the need for cryogenic cooling and complicated signal amplification. This in turn may enable the creation of a less complicated and expensive spectroscopic platform, with applications in, for example, diagnostic medicine, greenhouse gas monitoring, gas alarms, detection of explosives or drugs, industrial process monitoring, etc.

Figure 11:
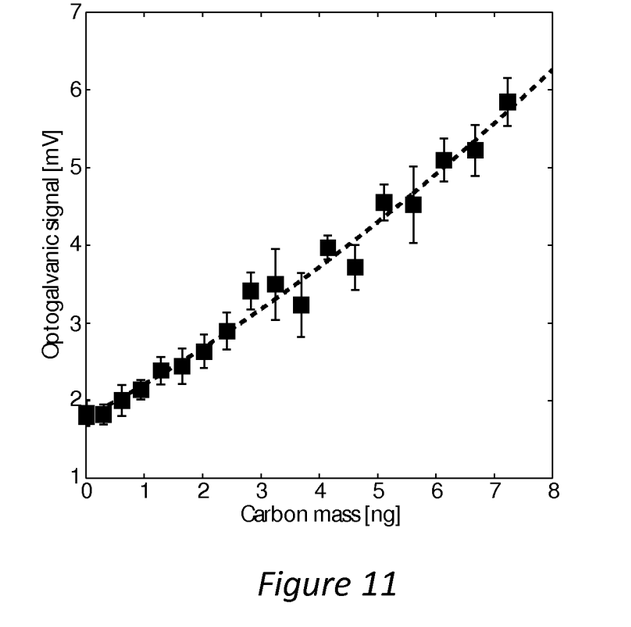
FIG. 11 is a calibration curve for an extracavity optogalvanic measurement employing a stripline split-ring resonator as a sample cell.

FIG. 11 shows results from extracavity OGS with a stripline split-ring resonator sample cell. FIG. 12 depicts two such stripline split-ring resonator sample cells with the windows 8 removed and illustrating the electric 23, 24 and fluidic 9 connections, with the parts corresponding to the device of FIG. 8.

The miniaturized plasma source according to the embodiments of the invention can be made of a number of materials. The dielectric materials 3 may be, for example, a polymer, glass, ceramic, glass ceramic, combinations thereof, etc. For example, the dielectric may be printed circuit board (e.g., polymer), zirconium oxide, hafnium oxide or silicon, and may preferably be aluminum oxide, or fiberglass-reinforced hydrocarbon ceramic laminate. The electrically conductive material for the ground plane may be a metal or a metal alloy, e.g., platinum, silver, nickel or aluminum, and may preferably be copper or gold. The windows may be made of a material that is transparent to the radiation beam, such as diamond, silicon, or silicon dioxide, and may preferably be zinc selenide or germanium. The plasma probes and the connections may be made of any electrically conductive material, such as a metal or metal alloy, e.g., copper or aluminum, and preferably gold or platinum.

In various embodiments, the radius of the split-ring resonator 2' may be between 2.7 mm and 60 mm, to enable resonance between 0.5 GHz and 6 GHz for different materials, and may preferably be between 5.4 mm and 6.5 mm, which may enable resonance around 2.5 GHz, where a wide variety of electronics components is currently available. The width of the hole 5 through the gap 2A of the split-ring resonator, and the distance between the ends of the split ring, may be between 0.1 mm and 10 mm, to enable different kinds of fluidic and laser spectroscopy applications, and may preferably be between 1 mm and 5 mm, where the plasma is adequately simple to ignite in a pressure range typically being between 10 and 10000 Pa. The length of the plasma probes may be between 0.05 mm and 5 mm, and is preferably between 0.25 mm and 1.25 mm, i.e., 25% of the preferred width of the hole. The plasma probes 2" may be made of any kind of conducting wire which may have a radius of less than 0.05 mm to enable the wire to be wedged between the stripline split-ring resonator 2" and the adjacent dielectric material 3. The plasma probes 2" may preferably be bond wires compatible with standard MEMS wire bonding. The windows 8 may be coated with an antireflective coating and may preferably be mounted at the Brewster angle of the laser beam.

The split ring resonator plasma source of the various embodiments may be fabricated in a number of ways. For example, the plasma source may be fabricated by joining of two essentially flat but structured or patterned members, and could also be successively formed by adding layers (structured or not) in a bottom up approach, or cast, or built up voxel by voxel, or by a combination of any of these methods. From this follows, e.g., that: "sandwiched" does not necessarily mean clamping, or even assembled in place, the embedment can be achieved, for example, by molding. Moreover, for the benefit of integration with other components, the split ring resonator plasma source may have a generally flat shape, such as shown in FIG. 12, although it will be understood that the overall shape of the device need not be flat. Various embodiments of the split ring resonator plasma source could equally well be of a low aspect ratio (almost spherical or cubic) or, the opposite, of high aspect ratio (for instance tubular).

Apart from those mentioned above, the stripline split-ring resonator 1 could be used in a number of applications. In fact, any application requiring a substance to be transported from one volume into another, while going through some kind of ionization process would benefit from the invention, since it could be used as an ionizing aperture or orifice. Examples of such applications are chemical analysis, sterilization, and activation of substances.

The foregoing description of the invention has been presented for purposes of illustration and description. It is not intended to be exhaustive or to limit the invention to the precise form disclosed, and modifications and variations are possible in light of the above teachings or may be acquired from practice of the invention. The description was chosen in order to explain the principles of the invention and its practical application. It is intended that the scope of the invention be defined by the claims appended hereto, and their equivalents.

| Parts List | | |
|---|---|---|
| 1. SSRR | 1'. SSRR in laser spectroscopy | 1". SSRR in ICOGS |
| 2. Ground plane | 2. Split-ring resonator | 2". Plasma probe pads |
| 201. Split-ring portion | 2A. Gap in split-ring portion | |
| 3. Dielectric Material | 3'. surrounding dielectric env. | |
| 4. Countersink | | |
| 5. Hole | | |
| 6. Plasma | | |
| 7. Laser beam | | |
| 8. Window | | |
| 9. Fluidic system | | |
| 10. Sample cell | | |
| 11. Plasma probes | | |
| 12. Detector | | |
| 13. Power source | 13'. Laser power source | |
| 14. Laser cavity | | |
| 15. Laser | 15'. Reference laser | |

-continued

Parts List

16. Laser medium
17. Analyte source
18. Vacuum
19. Shutter          19'. Reference shutter
20. Modulator
21. Signal processing
22. Reflector        22'. Reflector.   22''. Reflector.   22'''. Reflector
23. Probe connection
24. Power source connection
25. Optical cavity
101. First piece of SSRR
103. Second piece of SSRR
105. First side of split-ring resonator
107. Second side of split-ring resonator
109. First side of first dielectric material
111. Second side of first dielectric material
113. First side of second dielectric material
115. Second side of second dielectric material

What is claimed is:

1. A plasma source, comprising:
a split-ring resonator comprising a gap and having a first side and a second side;
a first dielectric material having a first side facing the first side of the split-ring resonator and a second side opposite to the first side;
a first electrically conductive ground plane facing the second side of the first dielectric material;
a second dielectric material having a first side facing the second side of the split-ring resonator;
a second electrically conductive ground plane facing the second side of the second dielectric material;
at least one probe located in the gap configured to measure at least one electrical property affected by an interaction between electromagnetic radiation and a plasma in the gap;
a probe connection configured to connect the at least one probe to a detector; and
a power source connection separate from the probe connection configured to connect a power source to the split-ring resonator.

2. The plasma source according to claim 1, wherein:
the first side of the first dielectric material contacts the first side of the split-ring resonator;
the second side of the first dielectric material contacts the first electrically conductive ground plane;
the first side of the second dielectric material contacts the second side of the split-ring resonator;
the second side of the second dielectric material contacts the second electrically conductive ground plane; and
the probe connection contacts at least one side of at least one of the first and second dielectric materials.

3. The plasma source according to claim 1, wherein:
the split-ring resonator comprises a ring having the gap;
the first dielectric material and the second dielectric material comprise respective first and second electrically insulating plates; and
the first and the second electrically conductive ground planes each comprises a metal or metal alloy layer located on a second side of the respective first and second electrically insulating plates.

4. The plasma source according to claim 3, further comprising a hole which exposes the gap and which extends through at least the first dielectric material and the first ground plane.

5. The plasma source according to claim 4, wherein the hole further extends through the second dielectric material and the second ground plane to expose the gap from two sides.

6. The plasma source according to claim 5, wherein the first dielectric material comprises a first substrate supporting the first ground plane and the split-ring resonator, and the second dielectric material comprises a second substrate supporting the second ground plane and having a countersink groove in which at least a portion of the split-ring resonator is accommodated.

7. The plasma source according to claim 1, further comprising a recess located at least one of beneath and above the gap and in proximity to the gap, wherein the recess is formed in at least one of the first dielectric and the second dielectric materials and is configured to minimize erosion, contamination and disturbances from electromagnetic interaction between the plasma and the plasma source.

8. The plasma source according to claim 1, further comprising a pathway in at least one of the first dielectric material and the second dielectric material to make the gap accessible to a fluid or gas, the pathway extending from outside the plasma source to the gap.

9. The plasma source according to claim 8, wherein the pathway is configured to be connected to an analyte reservoir containing an analyte comprising the fluid or the gas.

10. The plasma source according to claim 9, wherein the gap is fluidically confined.

11. The plasma source according to claim 10, wherein the gap is fluidically confined by at least one optically transparent member to allow for radiation entering, exiting or transiting the gap while maintaining the fluidical confinement.

12. The plasma source according to claim 5, wherein the hole comprises a straight radiation pathway which enables access through the gap along a line of sight and which enables a radiation beam, a probe or a sample administrator to transit the gap.

13. The plasma source according to claim 4, wherein:
the split-ring resonator comprises a split-ring portion that includes the gap between first and second ends of the split-ring portion and having a substantially circular shape when viewed from above;
the split-ring portion has a radius between 2.7 mm and 60 mm;

a width of the gap between the first and second ends of the split-ring portion is between 0.1 mm and 10 mm; and
a width of the hole is between 0.1 mm and 10 mm.

14. An optogalvanic spectroscopy system comprising:
a laser;
a split ring resonator plasma source; and
a probe configured to measure at least one electrical property affected by an interaction between optical radiation from the laser and an analyte located in a plasma generated by the split ring resonator plasma source.

15. The system of claim 14, wherein the split-ring resonator plasma source comprises:
a split-ring resonator comprising a gap and having a first side and a second side;
a first dielectric material having a first side facing the first side of the split-ring resonator and a second side opposite to the first side;
a first electrically conductive ground plane facing the second side of the first dielectric material;
a second dielectric material having a first side facing the second side of the split-ring resonator;
a second electrically conductive ground plane facing the second side of the second dielectric material,
and wherein the probe is located in the gap and is configured to monitor an electrical property of a plasma in the gap;
a probe connection is configured to connect the probe to a detector; and
a power source connection separate from the probe connection is configured to connect a power source to the split-ring resonator.

16. The system of claim 14, wherein the system comprises an intracavity optogalvanic spectroscopy system in which the plasma source is located in a cavity of the laser.

17. The system of claim 14, wherein the system comprises an extracavity optogalvanic spectroscopy system in which the plasma source is located outside of a cavity of the laser.

18. The system of claim 14, wherein the plasma source is located inside an optical cavity that is located outside of an optical cavity of the laser, wherein radiation from the laser is transmitted into the optical cavity containing the plasma source.

19. The system of claim 18, wherein the system comprises at least one of a cavity ring-down spectroscopy (CRDS) system, an integrated cavity output spectroscopy (ICOS) system and an off-axis integrated cavity output spectroscopy (OA-ICOS) system.

20. An optogalvanic spectroscopy method, comprising:
generating a plasma in a gap of a split-ring resonator plasma source, such that an analyte is located in the plasma in the gap;
providing laser radiation through the analyte located in the plasma in the gap; and
detecting at least one electrical property affected by an interaction between the laser radiation and the analyte located in the plasma.

21. The method of claim 20, wherein the split-ring resonator plasma source comprises:
a split-ring resonator comprising the gap and having a first side and a second side;
a first dielectric material having a first side facing the first side of the split-ring resonator and a second side opposite to the first side;
a first electrically conductive ground plane facing the second side of the first dielectric material;
a second dielectric material having a first side facing the second side of the split-ring resonator; and
a second electrically conductive ground plane facing the second side of the second dielectric material.

22. The method of claim 20, further comprising:
providing power from a power source through a power source connection to the split-ring resonator to generate the plasma; and
detecting the at least one electrical signal using at least one probe located in the gap and connected to a detector using a probe connection separate from the power source connection.

23. The method of claim 20, wherein the optogalvanic spectroscopy method comprises at least one of intracavity optogalvanic spectroscopy, extracavity optogalvanic spectroscopy, cavity ring-down spectroscopy, integrated cavity output spectroscopy, and off-axis integrated cavity output spectroscopy.

* * * * *